United States Patent
Lee

(10) Patent No.: US 10,662,143 B2
(45) Date of Patent: May 26, 2020

(54) MODIFICATION MONOMER, MODIFIED CONJUGATED DIENE-BASED POLYMER INCLUDING THE SAME AND METHOD FOR PREPARING THE POLYMER

(71) Applicant: LG Chem, Ltd., Seoul (KR)

(72) Inventor: Ro Mi Lee, Daejeon (KR)

(73) Assignee: LG Chem, Ltd. (KR)

( * ) Notice: Subject to any disclaimer, the term of this patent is extended or adjusted under 35 U.S.C. 154(b) by 183 days.

(21) Appl. No.: 15/762,340

(22) PCT Filed: Oct. 18, 2017

(86) PCT No.: PCT/KR2017/011550
§ 371 (c)(1),
(2) Date: Mar. 22, 2018

(87) PCT Pub. No.: WO2018/088710
PCT Pub. Date: May 17, 2018

(65) Prior Publication Data
US 2019/0071390 A1    Mar. 7, 2019

(30) Foreign Application Priority Data

Nov. 14, 2016 (KR) .......... 10-2016-0151390
Jul. 31, 2017 (KR) .......... 10-2017-0097141

(51) Int. Cl.
| | | |
|---|---|---|
| C08F 236/10 | (2006.01) |
| C07C 211/22 | (2006.01) |
| C08L 15/00 | (2006.01) |
| B60C 1/00 | (2006.01) |
| C07F 7/18 | (2006.01) |
| C08C 19/22 | (2006.01) |
| C08C 19/25 | (2006.01) |
| C08C 19/44 | (2006.01) |

(52) U.S. Cl.
CPC .......... *C07C 211/22* (2013.01); *B60C 1/0016* (2013.01); *C07F 7/1804* (2013.01); *C08C 19/22* (2013.01); *C08C 19/25* (2013.01); *C08C 19/44* (2013.01); *C08F 236/10* (2013.01); *C08L 15/00* (2013.01); *B60C 1/00* (2013.01); *Y02T 10/862* (2013.01)

(58) Field of Classification Search
CPC ....... C07C 211/22; B60C 1/00; C08F 236/10; C08C 19/22; C08C 19/25; C08C 19/44
See application file for complete search history.

(56) References Cited

U.S. PATENT DOCUMENTS

| | | | | |
|---|---|---|---|---|
| 2,964,563 A | * | 12/1960 | Bost | ...... C07C 209/90 564/2 |
| 4,338,428 A | * | 7/1982 | Alberino | ...... C08G 18/678 264/328.1 |
| 4,342,841 A | | 8/1982 | Alberino et al. | |
| 4,397,994 A | | 8/1983 | Takeuchi et al. | |
| 4,536,490 A | | 8/1985 | Regelman | |
| 4,703,099 A | * | 10/1987 | Regelman | ...... C07C 255/00 521/128 |
| 5,112,920 A | | 5/1992 | Haag | |
| 5,240,976 A | * | 8/1993 | Horsey | ...... C08K 5/37 524/93 |
| 5,492,954 A | * | 2/1996 | Babiarz | ...... C07C 211/55 524/241 |
| 5,961,902 A | | 10/1999 | Ishitoya et al. | |
| 6,933,358 B2 | | 8/2005 | Halasa et al. | |
| 6,936,669 B2 | | 8/2005 | Halasa et al. | |
| 2014/0371383 A1 | | 12/2014 | Hayata et al. | |
| 2016/0053059 A1 | * | 2/2016 | Kim | ...... B60C 1/0016 525/102 |
| 2016/0096947 A1 | | 4/2016 | Ono | |
| 2016/0194411 A1 | | 7/2016 | Lee et al. | |
| 2018/0244892 A1 | * | 8/2018 | Lee | ...... C08L 15/00 |
| 2020/0055898 A1 | * | 2/2020 | Mahr | ...... C07K 14/7051 |

FOREIGN PATENT DOCUMENTS

| | | |
|---|---|---|
| EP | 1457501 A1 | 9/2004 |
| EP | 2749575 A1 | 7/2014 |
| EP | 3059259 A1 | 8/2016 |
| JP | H06271706 A | 9/1994 |
| JP | 2003171418 A | 6/2003 |
| JP | 2011219701 A | 11/2011 |
| JP | 2015000922 A | 1/2015 |
| JP | 2016531181 A | 10/2016 |
| WO | 96030185 A1 | 10/1996 |
| WO | 2013031599 A1 | 3/2013 |
| WO | 2015056878 A1 | 4/2015 |

OTHER PUBLICATIONS

Search report from International Application No. PCT/KR2017/011550, dated Jan. 24, 2018.
Extended European Search Report including Written Opinion for Application No. EP178446472 dated Oct. 9, 2018.

* cited by examiner

*Primary Examiner* — Margaret G Moore
(74) *Attorney, Agent, or Firm* — Lerner, David, Littenberg, Krumholz & Mentlik, LLP

(57) ABSTRACT

The present invention relates to a modification monomer and a modified conjugated diene-based polymer including the same, and more particularly, provides a modification monomer represented by Formula 1 and a modified conjugated diene-based polymer including a repeating unit derived therefrom.

13 Claims, No Drawings

MODIFICATION MONOMER, MODIFIED CONJUGATED DIENE-BASED POLYMER INCLUDING THE SAME AND METHOD FOR PREPARING THE POLYMER

CROSS-REFERENCE TO RELATED APPLICATIONS

The present application is a national phase entry under 35 U.S.C. § 371 of International Application No. PCT/KR2017/011550 filed Oct. 18, 2017, which claims priority from Korean Patent Application No. 10-2016-0151390, filed on Nov. 14, 2016, and Korean Patent Application No. 10-2017-0097141, filed on Jul. 31, 2017, all of which are incorporated herein by reference.

TECHNICAL FIELD

The present invention relates to a modification monomer, and more particularly, to a modification monomer having small steric hindrance and containing two or more amine groups, a modified conjugated diene-based polymer including a repeating unit derived therefrom, and a method for preparing the polymer.

BACKGROUND ART

According to the recent demand for cars having a low fuel consumption ratio, a modified conjugated diene-based polymer having modulational stability represented by wet skid resistance as well as low rolling resistance, and excellent abrasion resistance and tensile properties is required as a rubber material for tires.

In order to reduce the rolling resistance of tires, there is a method of reducing hysteresis loss of vulcanized rubber, and rebound resilience at 50° C. to 80° C., tan δ, Goodrich heating, or the like is used as an evaluation index of the vulcanized rubber. That is, it is desirable to use a rubber material having high rebound resilience at the above temperature or a low tan δ value or Goodrich heating.

Natural rubbers, polyisoprene rubbers, or polybutadiene rubbers are known as rubber materials having low hysteresis loss, but these rubbers have a limitation of low wet skid resistance. Thus, recently, modified conjugated diene-based polymers or copolymers such as styrene-butadiene rubbers (hereinafter, referred to as "SBR") and butadiene rubbers (hereinafter, referred to as "BR"), are prepared by emulsion polymerization or solution polymerization to be used as rubbers for tires. Among these polymerization methods, the greatest advantage of the solution polymerization in comparison to the emulsion polymerization is that the vinyl structure content and the styrene content, which specify physical properties of the rubber, may be arbitrarily adjusted and its molecular weight and physical properties may be controlled by coupling or modification. Thus, the SBR prepared by the solution polymerization is widely used as a rubber material for tires because it is easy to change a structure of the finally prepared SBR or BR, and movement of chain terminals may be reduced and a coupling force with a filler such as silica and carbon black may be increased by coupling or modification of the chain terminals.

If the solution-polymerized SBR is used as the rubber material for tires, since a glass transition temperature of the rubber is increased by increasing the vinyl content in the SBR, physical properties such as running resistance and braking force, required for tires may be controlled, and fuel consumption may also be reduced by appropriately adjusting the glass transition temperature. The solution-polymerized SBR is prepared by using an anionic polymerization initiator and is being used by coupling or modifying the chain terminals of the polymer thus formed using various modifiers. For example, U.S. Pat. No. 4,397,994 discloses a method of coupling active anions of the chain terminals of a polymer obtained by polymerizing styrene-butadiene using alkyllithium which is a monofunctional initiator in a non-polar solvent, using a binder such as a tin compound.

Meanwhile, carbon black and silica are being used as a reinforcing filler of a tire tread, wherein, if the silica is used as the reinforcing filler, low hysteresis loss and wet skid resistance may be improved. However, since the silica having a hydrophilic surface has a low affinity with a rubber in comparison to the carbon black having a hydrophobic surface, dispersibility may be poor, and thus, there is a need to use a separate silane coupling agent to improve the dispersibility or provide coupling between the silica and the rubber. Therefore, attempt of introducing a monomer having affinity with silica or introducing a functional group having affinity or reactivity with silica into the terminal of a rubber molecule is being performed, but its effect is insufficient. For example, U.S. Pat. Nos. 6,933,358 and 6,936,669 disclose techniques on introducing a functional monomer of a styrene derivative containing a cyclic amine group. However, when additionally introducing a functional group having affinity or reactivity with silica to the terminal of a rubber molecule to which the monomer has been introduced, defects of decreasing efficiency of reaction or coupling arises due to steric hindrance.

DISCLOSURE OF THE INVENTION

Technical Problem

The present invention has been devised to solve the above-mentioned problems of the conventional technique, and an object of the present invention is to provide a modification monomer having small steric hindrance and containing two or more amine groups.

Another object of the present invention is to provide a modified conjugated diene-based polymer with a high viscosity, having excellent rolling resistance and increased reaction efficiency or coupling efficiency with a modifier by including a repeating unit derived from the modification monomer.

Further another object of the present invention is to provide a method for preparing the modified conjugated diene-based polymer.

Technical Solution

To solve the above-described tasks, according to an embodiment of the present invention, there is provided a modification monomer represented by the following Formula 1:

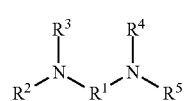

[Formula 1]

In Formula 1, $R^1$ may be a divalent hydrocarbon group of 1 to 10 carbon atoms, a heteroatom-containing divalent hydrocarbon group of 1 to 10 carbon atoms, or a linker represented by the following Formula 2, $R^2$ to $R^5$ may be each independently hydrogen, a monovalent hydrocarbon group of 1 to 10 carbon atoms, or a heteroatom-containing monovalent hydrocarbon group of 1 to 10 carbon atoms, and one or more of $R^1$ to $R^5$ are required to be hydrocarbon groups including an unsaturated bond, where if $R^2$ to $R^5$ do not include an unsaturated bond, $R^1$ may be required to be a linker represented by the following Formula 2:

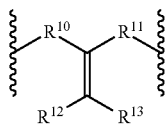

[Formula 2]

In Formula 2, $R^{10}$ and $R^{11}$ may be each independently a single bond, a divalent hydrocarbon group of 1 to 5 carbon atoms, or a heteroatom-containing divalent hydrocarbon group of 1 to 5 carbon atoms, and $R^{12}$ and $R^{13}$ may be each independently hydrogen, a monovalent hydrocarbon group of 1 to 5 carbon atoms, or a heteroatom-containing monovalent hydrocarbon group of 1 to 5 carbon atoms.

In addition, the present invention provides a modified conjugated diene-based polymer including a repeating unit derived from the modification monomer, and a method for preparing the same.

Advantageous Effects

In case of polymerizing including a modification monomer according to the present invention to prepare a modified conjugated diene-based polymer including a repeating unit derived from the modification monomer, the modified conjugated diene-based polymer has excellent rolling resistance properties, and particularly, an increased modification ratio or coupling efficiency during performing additional modification reaction or coupling reaction with a modifier, and has effect of showing high viscosity.

BEST MODE FOR CARRYING OUT THE INVENTION

Hereinafter, the present invention will be described in more detail in order to assist the understanding of the present invention.

It will be understood that words or terms used in the description and claims of the present invention shall not be interpreted as the meaning defined in commonly used dictionaries. It will be further understood that the words or terms should be interpreted as having a meaning that is consistent with their meaning of the technical idea of the invention, based on the principle that an inventor may properly define the meaning of the words or terms to best explain the invention.

In the present invention, the term "modification monomer" may mean a comonomer which is capable of being copolymerized with a conjugated diene-based monomer during polymerizing a conjugated diene-based polymer, and may mean that the comonomer includes a modification functional group for modifying the properties of a conjugated diene-based polymer. The modification monomer may be, for example, a modification monomer constituting the repeating unit of a modified conjugated diene-based polymer, and in this case, effects such that rolling resistance is excellent, steric hindrance is insignificant, and thus, effi- ciency of a modification reaction or a coupling reaction with an additionally introduced modifier is very excellent, are achieved.

In the present invention, the term "derived unit" and "derived functional group" may represent a component or a structure comes from a certain material, or the material itself.

The modification monomer according to the present invention may be a modification monomer represented by the following Formula 1:

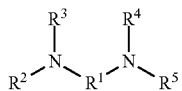

[Formula 1]

In Formula 1, $R^1$ may be a divalent hydrocarbon group of 1 to 10 carbon atoms, a heteroatom-containing divalent hydrocarbon group of 1 to 10 carbon atoms, or a linker represented by the following Formula 2, $R^2$ to $R^5$ may be each independently hydrogen, a monovalent hydrocarbon group of 1 to 10 carbon atoms, or a heteroatom-containing monovalent hydrocarbon group of 1 to 10 carbon atoms, and one or more of $R^1$ to $R^5$ are required to be hydrocarbon groups including an unsaturated bond, where if $R^2$ to $R^5$ do not include an unsaturated bond, $R^1$ may be required to be a linker represented by the following Formula 2:

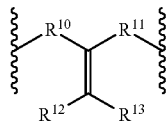

[Formula 2]

In Formula 2, $R^{10}$ and $R^{11}$ may be each independently a single bond, a divalent hydrocarbon group of 1 to 5 carbon atoms, or a heteroatom-containing divalent hydrocarbon group of 1 to 5 carbon atoms, and $R^{12}$ and $R^{13}$ may be each independently hydrogen, a monovalent hydrocarbon group of 1 to 5 carbon atoms, or a heteroatom-containing monovalent hydrocarbon group of 1 to 5 carbon atoms.

In a particular embodiment, in Formula 1, $R^1$ may be a divalent hydrocarbon group of 1 to 5 carbon atoms, a heteroatom-containing divalent hydrocarbon group of 1 to 5 carbon atoms, or a linker represented by Formula 2 above, $R^2$ to $R^5$ may be each independently hydrogen, a monovalent hydrocarbon group of 1 to 5 carbon atoms, or a heteroatom-containing monovalent hydrocarbon group of 1 to 5 carbon atoms, and one or more of $R^1$ to $R^5$ are required to be a hydrocarbon group including an unsaturated bond, where if $R^2$ to $R^5$ do not include an unsaturated bond, $R^1$ may be required to be a linker represented by Formula 2, and in Formula 2, $R^{10}$ and $R^{11}$ may be each independently a single bond, or a divalent hydrocarbon group of 1 to 3 carbon atoms, and $R^{12}$ and $R^{13}$ may be each independently hydrogen, or a monovalent hydrocarbon group of 1 to 5 carbon atoms.

In a more particular embodiment, in Formula 1, $R^1$ may be a linker represented by Formula 2 above, and $R^2$ to $R^5$ may be each independently hydrogen, or a monovalent hydrocarbon group of 1 to 5 carbon atoms, and in Formula 2, $R^{10}$ and $R^{11}$ may be each independently a single bond, or a divalent hydrocarbon group of 1 to 3 carbon atoms, and $R^{12}$ and $R^{13}$ may be each independently hydrogen, or a monovalent hydrocarbon group of 1 to 3 carbon atoms.

In this case, two or more amine groups are included in the modification monomer and effects such that affinity with a filler is excellent, and coupling efficiency during additional modification reaction or coupling reaction with a modifier is excellent due to insignificant steric hindrance, are achieved.

In addition, the modification monomer includes one or more unsaturated bond, and this unsaturated bond may be a polymerization reactive functional group for participating in polymerization as a monomer during performing anionic polymerization of a conjugated diene-based monomer, and the unsaturated bond may be, for example, a double bond or a triple bond, particularly, a double bond. In another embodiment, the unsaturated bond may be an unsaturated bond between carbon-carbon and an unsaturated bond between carbon-nitrogen, particularly, an unsaturated bond between carbon-carbon.

The heteroatom may be, for example, one kind of heteroatom selected from the group consisting of a nitrogen atom, an oxygen atom and a sulfur atom, and the heteroatom-containing divalent hydrocarbon group or monovalent hydrocarbon group may include one to three, one or two, or one of the heteroatom.

In the present invention, the term "monovalent hydrocarbon group" may mean a monovalent atomic group in which carbon and hydrogen are bonded, such as a monovalent alkyl group, alkenyl group, alkynyl group, cycloalkyl group, cycloalkyl group including one or more unsaturated bonds, and aryl group.

In the present invention, the term "divalent hydrocarbon group" may mean a divalent atomic group in which carbon and hydrogen are bonded, such as a divalent alkylene group, alkenylene group, alkynylene group, cycloalkylene group, cycloalkylene group including one or more unsaturated bonds and arylene group.

According to an embodiment of the present invention, the modification monomer represented by Formula 1 may be represented by the following Formula 1-1:

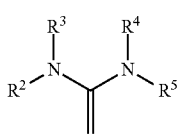

[Formula 1-1]

In Formula 1-1, the definition on each substituent is the same as defined above.

In a particular embodiment, the modification monomer represented by Formula 1-1 may be one or more selected from the group consisting of the following Formulae 1a to 1e:

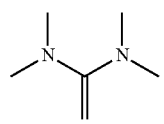

[Formula 1a]

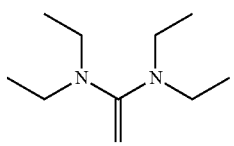

[Formula 1b]

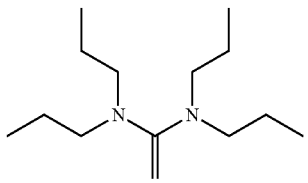

[Formula 1c]

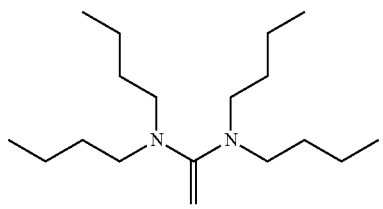

[Formula 1d]

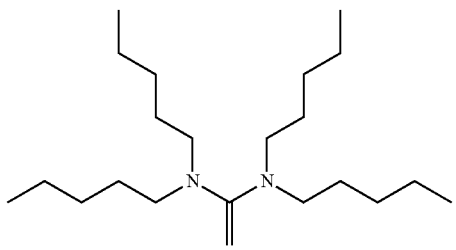

[Formula 1e]

The modified conjugated diene-based polymer according to the present invention may include a repeating unit derived from a conjugated diene-based monomer and a repeating unit derived from a modification monomer represented by the following Formula 1:

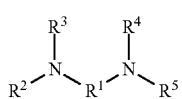

[Formula 1]

The definition on each substituent of Formula 1 is the same as defined above.

The repeating unit of the conjugated diene-based monomer may mean a repeating unit formed by the conjugated diene-based monomer during polymerization, and the conjugated diene-based monomer may be, for example, one or more selected from the group consisting of 1,3-butadiene, 2,3-dimethyl-1,3-butadiene, piperylene, 3-butyl-1,3-octadiene, isoprene, 2-phenyl-1,3-butadiene, and 2-halo-1,3-butadiene (halo means halogen atom).

Meanwhile, a modified conjugated diene-based copolymer may be, for example, a copolymer further including a repeating unit derived from an aromatic vinyl monomer together with the repeating unit derived from the conjugated diene-based monomer and the repeating unit derived from the modification monomer.

The repeating unit derived from the aromatic vinyl based monomer may mean a repeating unit formed by an aromatic vinyl monomer during polymerization, and the aromatic vinyl monomer may include, for example, one or more selected from the group consisting of styrene, α-methylstyrene, 3-methylstyrene, 4-methylstyrene, 4-propylstyrene, 1-vinylnaphthalene, 4-cyclohexylstyrene, 4-(p-methylphenyl)styrene, and 1-vinyl-5-hexylnaphthalene.

A modified conjugated diene-based polymer including the repeating unit derived from the conjugated diene-based monomer, the repeating unit derived from the modification monomer and the repeating unit derived from the aromatic vinyl monomer may be, for example, a block copolymer forming each block in a polymer, or a random copolymer in which each repeating unit is arranged in disorder.

According to an embodiment of the present invention, the repeating unit derived from the modification monomer may be included at the terminal part of the modified conjugated diene-based polymer, and in this case, the terminal part of the modified conjugated diene-based polymer is end-capped with the repeating unit derived from the modification monomer, thereby achieving excellent affinity with a filler and excellent coupling efficiency during additional modification reaction or coupling reaction with a modifier due to insignificant steric hindrance.

In another embodiment, the modified conjugated diene-based polymer may include the repeating unit derived from the modification monomer at the terminal part of the random copolymer in which the repeating unit derived from the conjugated diene-based monomer and the repeating unit derived from the aromatic vinyl monomer are arranged in disorder.

Meanwhile, the repeating unit derived from the modification monomer may be included by 0.01 wt % to 10 wt %, 0.05 wt % to 8 wt %, or 0.1 wt % to 5 wt % based on the total weight of the repeating unit derived from each monomer which constitutes the modified conjugated diene-based polymer, and within this range, effects of excellent rolling resistance, wet skid resistance and abrasion resistance may be achieved.

According to an embodiment of the present invention, the modified conjugated diene-based polymer may include a functional group derived from a modifier at the terminal thereof. The functional group derived from a modifier may mean a functional group in a polymer, which is produced by the reaction of the active part of a conjugated diene-based polymer with a modifier, and from the functional group, effects of improving the dispersibility and processability of a conjugated diene-based polymer and increasing mechanical properties such as rolling resistance and wet skid resistance may be achieved.

The modifier according to an embodiment of the present invention may be an alkoxysilane-based modifier, and in a particular embodiment, the alkoxysilane-based modifier may be a modifier represented by the following Formula 3:

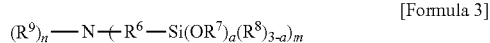
[Formula 3]

In Formula 3, $R^6$ may be an alkylene group of 1 to 10 carbon atoms, $R^7$ and $R^8$ may be each independently an alkyl group of 1 to 10 carbon atoms, $R^9$ may be hydrogen, an alkyl group of 1 to 10 carbon atoms, or a divalent, trivalent, or tetravalent alkylsilyl group which is unsubstituted or substituted with an alkyl group of 1 to 10 carbon atoms, a and m may be each independently an integer selected from 1 to 3, and n may be an integer selected from 0 to 2, where if n is 2, a plurality of $R^9$ groups may be the same or different.

In a particular embodiment, in Formula 3, $R^7$ and $R^8$ may be each independently hydrogen, or an alkyl group of 1 to 5 carbon atoms, $R^9$ may be hydrogen, or an alkyl group of 1 to 5 carbon atoms, $R^6$ may be an alkylene group of 1 to 5 carbon atoms, a may be an integer of 2 or 3, and m and n may be each independently an integer of 1 or 2, where m+n=3 may be satisfied, and if n is 2, a plurality of $R^9$ groups may be the same or different.

According to an embodiment of the present invention, the modifier represented by Formula 3 may be one selected from the group consisting of the modifiers represented by the following Formulae 3-1 to 3-27:

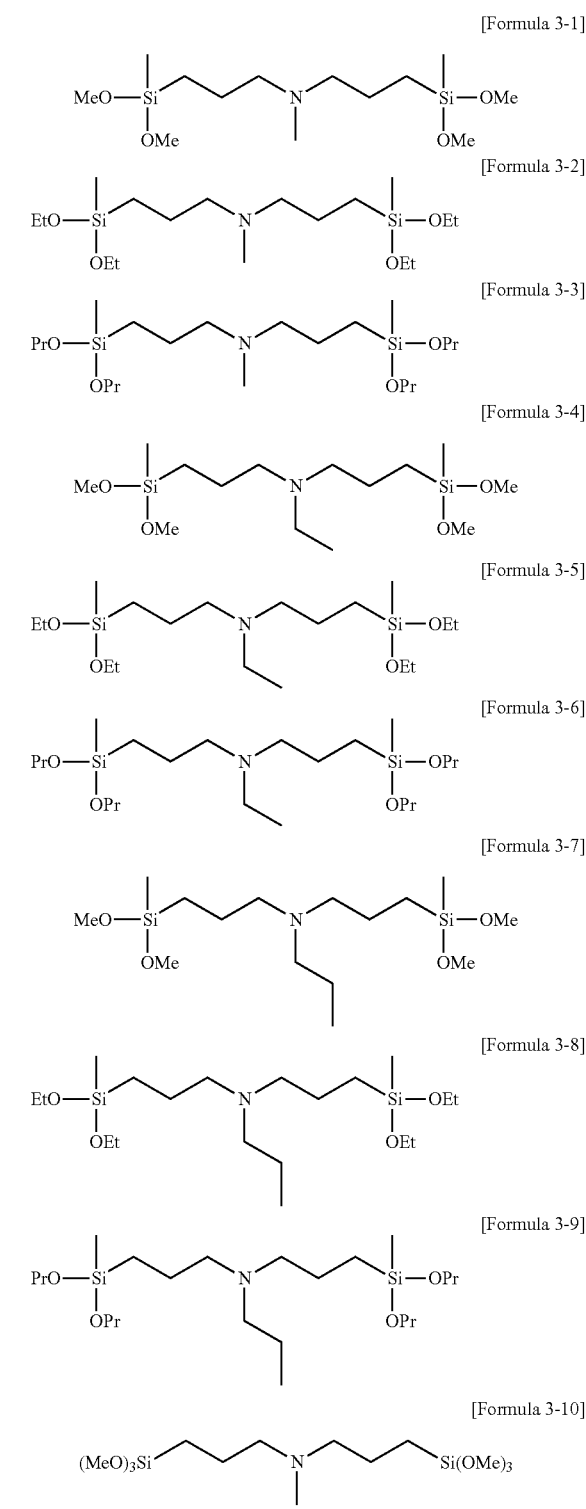

-continued

[Formula 3-11]
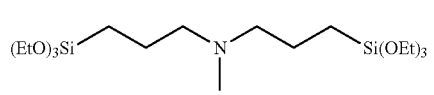

[Formula 3-12]
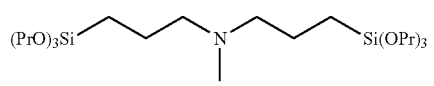

[Formula 3-13]
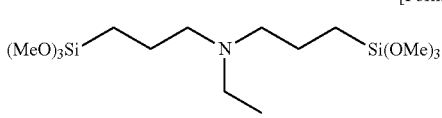

[Formula 3-14]
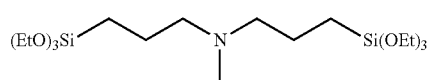

[Formula 3-15]
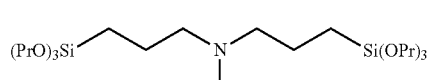

[Formula 3-16]
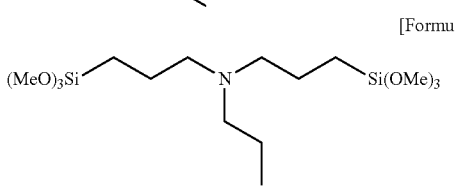

[Formula 3-17]
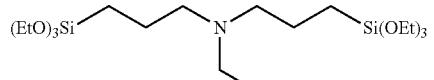

[Formula 3-18]
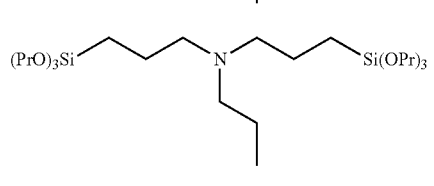

[Formula 3-19]
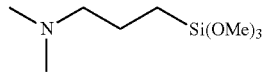

[Formula 3-20]
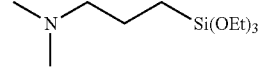

[Formula 3-21]
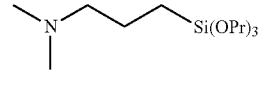

[Formula 3-22]
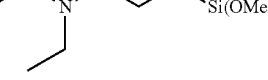

[Formula 3-23]
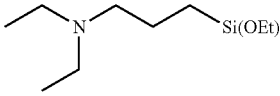

[Formula 3-24]
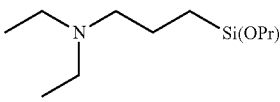

-continued

[Formula 3-25]
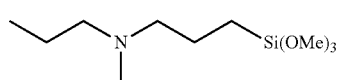

[Formula 3-26]
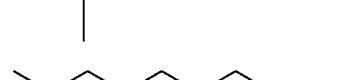

[Formula 3-27]
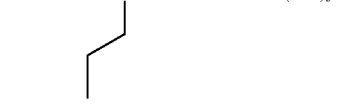

In Formulae 3-1 to 3-27 above, Me is a methyl group, Et is an ethyl group, and Pr is a propyl group.

In another embodiment, the modifier may be a modifier represented by the following Formula 4 or Formula 5:

[Formula 4]
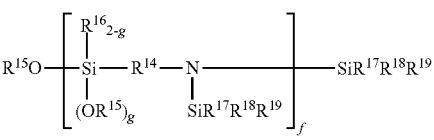

[Formula 5]
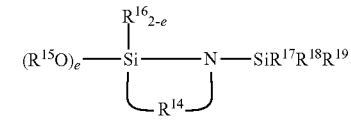

In Formulae 4 and 5 above, $R^{14}$ may be an alkylene group of 1 to 12 carbon atoms, $R^{15}$ and $R^{16}$ may be each independently an alkyl group of 1 to 20 carbon atoms or an aryl group, $R^{17}$, $R^{18}$ and $R^{19}$ may be each independently an alkyl group of 1 to 20 carbon atoms or an aryl group, or two thereof may be combined with each other to form a ring including a silicon atom to which two thereof are combined, e may be an integer of 1 to 2, g may be an integer of 1 to 2, and f may be an integer of 1 to 10.

In a particular embodiment, the modifier represented by Formula 4 or Formula 5 may be one selected from the group consisting of N,N-bis(trimethylsilyl)aminopropylmethyl-dimethoxysilane, 1-trimethylsilyl-2,2-dimethoxy-1-aza-2-silacyclopentane, N,N-bis(trimethylsilyl)aminopropyltrimethoxysilane, N,N-bis(trimethylsilyl) aminopropyltriethoxysilane, N,N-bis(trimethylsilyl) aminopropylmethyldiethoxysilane, N,N-bis(trimethylsilyl) aminoethyltrimethoxysilane, N,N-bis(trimethylsilyl) aminoethyltriethoxysilane, N,N-bis(trimethylsilyl) aminoethylmethyldimethoxysilane and N,N-bis(trimethylsilyl)aminoethylmethyldiethoxysilane.

Meanwhile, the modified conjugated diene-based polymer according to an embodiment of the present invention may have a number average molecular weight (Mn) of 10,000 g/mol to 2,000,000 g/mol, 100,000 g/mol to 1,000,000 g/mol, or 200,000 g/mol to 500,000 g/mol, and within this range, effects of excellent rolling resistance and wet skid resistance may be achieved. In another embodiment, the modified conjugated diene-based polymer may have molecular weight distribution (Mw/Mn) of 1.0 to 5.0, 1.2 to 3.0, or 1.5 to 2.5, and within this range, effect of excellent balance between physical properties may be achieved.

In another embodiment, the modified conjugated diene-based polymer may have mooney viscosity of 10 to 200, 10 to 100, or 20 to 80, and within this range, effects of excellent processability and productivity may be achieved.

In addition, the modified conjugated diene-based polymer may have a vinyl content of 10 wt % or more, 60 wt % or less, or 20 wt % to 50 wt %, and within this range, the glass transition temperature may be adjusted in an appropriate range, and effects of excellent rolling resistance, wet skid resistance and a low fuel consumption ratio may be achieved. Here, the vinyl content may mean the amount of not 1,4-added but 1,2-added conjugated diene-based monomer based on 100 wt % of a conjugated diene-based copolymer composed of a monomer having a vinyl group, an aromatic vinyl-based monomer and a modification monomer.

A method for preparing a modified conjugated diene-based polymer according to the present invention may include a step of polymerizing conjugated diene-based monomers, or an aromatic vinyl-based monomer and a conjugated diene-based monomer, in a hydrocarbon solvent comprising an organometal compound, to prepare an active polymer which is coupled with an alkali metal (S1); and a step of reacting the active polymer and a modification monomer represented by the following Formula 1 for end-capping a terminal of the active polymer with the modification monomer (S2):

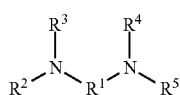

[Formula 1]

The definition of each substituent of Formula 1 is the same as defined above.

The hydrocarbon solvent is not specifically limited, but may be, for example, one or more selected from the group consisting of n-pentane, n-hexane, n-heptane, isooctane, cyclohexane, toluene, benzene and xylene.

According to an embodiment of the present invention, the organometal compound may be used in 0.01 mmol to 10 mmol, 0.05 mmol to 5 mmol, 0.1 mmol to 2 mmol, or 0.1 mmol to 1 mmol based on total 100 g of the monomer.

The organometal compound may be, for example, one or more selected from the group consisting of methyllithium, ethyllithium, propyllithium, n-butyllithium, s-butyllithium, t-butyllithium, hexyllithium, n-decyllithium, t-octyllithium, phenyllithium, 1-naphthyl lithium, n-eicosyl lithium, 4-butylphenyl lithium, 4-tolyl lithium, cyclohexyl lithium, 3,5-di-n-heptylcyclohexyl lithium, 4-cyclopentyl lithium, naphthyl sodium, naphthyl potassium, lithium alkoxide, sodium alkoxide, potassium alkoxide, lithium sulfonate, sodium sulfonate, potassium sulfonate, lithium amide, sodium amide, potassium amide, and lithium isopropylamide.

The polymerization of step (S1) may be performed by including a polar additive, and the polar additive may be added in an amount of 0.001 g to 50 g, 0.001 g to 10 g, or 0.005 g to 0.1 g based on total 100 g of the monomer. In addition, the polar additive may be one or more selected from the group consisting of tetrahydrofuran, ditetrahydrofurylpropane, diethyl ether, cycloamyl ether, dipropyl ether, ethylene dimethyl ether, diethyl glycol, dimethyl ether, tert-butoxy ethoxy ethane, bis(3-dimethylaminoethyl) ether, (dimethylaminoethyl) ethyl ether, trimethylamine, triethylamine, tripropylamine, and tetramethylethylenediamine, preferably, triethylamine or tetramethylethylenediamine, and may be the same as or different from a polar additive which may be injected during preparing the aminosilane-based compound. If the polar additive is included and conjugated diene-based monomers, or a conjugated diene-based monomer and an aromatic vinyl-based monomer are copolymerized, the reaction rates thereof may be compensated, and effect of inducing the easy formation of a random copolymer may be achieved.

The polymerization of step (S1) may be, for example, an anionic polymerization, and particularly, a living anionic polymerization by which an anionic active part is formed at the polymerization terminal through a propagation reaction by anions. In addition, the polymerization of step (S1) may be a polymerization with heating, an isothermal polymerization, or a polymerization at a constant temperature (adiabatic polymerization). Here, the polymerization at a constant temperature means a polymerization method including a step of polymerizing using self-generated heat of reaction without optionally applying heat after adding an organometal compound, and the polymerization with heating means a polymerization method including injecting the organometal compound and then, increasing the temperature by optionally applying heat. The isothermal polymerization means a polymerization method by which the temperature of a polymer is kept constant by increasing heat by applying heat or taking heat after adding the organometal compound. In addition, the polymerization of step (S1) may be conducted in a temperature range of −20° C. to 200° C., 0° C. to 150° C., or 10° C. to 120° C.

The active polymer prepared by step (S1) may mean a polymer in which a polymer anion and an organometallic cation are coupled.

According to an embodiment of the present invention, the modification monomer of step (S2) may be injected in an amount of 0.01 wt % to 10 wt %, 0.05 wt % to 8 wt %, or 0.1 wt % to 5 wt % based on the total monomer amount of the conjugated diene-based monomer and the modification monomer, or the conjugated diene-based monomer, the aromatic vinyl-based monomer and the modification monomer.

Meanwhile, the method for preparing a modified conjugated diene-based polymer of the present invention may include a step (S3) of reacting the active polymer which is end-capped in step (S2) with a modifier.

The modifier may be, for example, an alkoxysilane-based modifier, and particularly, the alkoxysilane-based modifier may be a modifier represented by the following Formula 3:

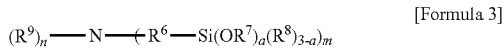

[Formula 3]

The definition on each substituent of Formula 3 is the same as defined above.

In another embodiment, the alkoxysilane-based modifier may be a modifier represented by the following Formula 4 or Formula 5:

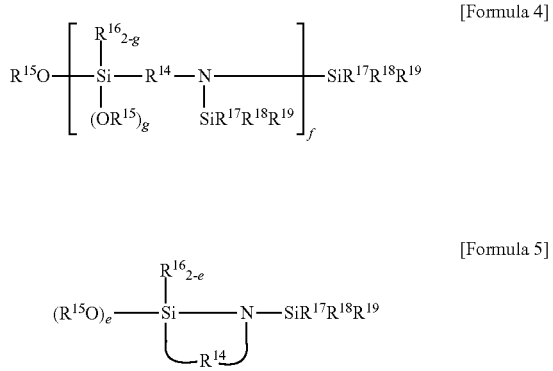

[Formula 4]

[Formula 5]

The definition on each substituent of Formulae 4 and 5 is the same as defined above.

According to an embodiment of the present invention, the molar ratio of the organometal compound and the modifier may be 1:0.1 to 1:10, or 1:0.3 to 1:3, and within this range, modification reaction may be performed with optimal performance, and a conjugated diene-based polymer with a high modification ratio may be obtained.

The reaction of step (S3) is a modification reaction for introducing a functional group derived from a modifier to the active polymer, and the reaction may be performed at 0° C. to 90° C. for 1 minute to 5 hours.

In addition, according to an embodiment of the present invention, the method for preparing a modified conjugated diene-based polymer may be performed by a batch type polymerization method or a continuous type polymerization method including one or more reactors.

The method for preparing a modified conjugated diene-based polymer may further include, for example, one or more steps among recovering and drying steps of a solvent and an unreacted monomer after step (S2) or step (S3) of the present invention according to need.

According to the present invention, a rubber composition including the modified conjugated diene-based polymer is provided.

The rubber composition may include the modified conjugated diene-based polymer in an amount of 10 wt % or more, 10 wt % to 100 wt %, or 20 wt % to 90 wt %. Within the range, effects of excellent mechanical properties such as tensile strength and abrasion resistance, and excellent balance between each of physical properties may be achieved.

In addition, the rubber composition may further include other rubber components, if necessary, in addition to the modified and conjugated diene-based polymer, and, in this case, the rubber component may be included in an amount of 90 wt % or less based on the total weight of the rubber composition. Particularly, the other rubber components may be included in an amount of 1 part by weight to 900 parts by weight based on 100 parts by weight of the modified and conjugated diene-based copolymer.

The rubber component may be, for example, a natural rubber or a synthetic rubber, particularly, a natural rubber (NR) including cis-1,4-polyisoprene; a modified natural rubber which is obtained by modifying or purifying a common natural rubber, such as an epoxidized natural rubber (ENR), a deproteinized natural rubber (DPNR), and a hydrogenated natural rubber; and a synthetic rubber such as a styrene-butadiene copolymer (SBR), a polybutadiene (BR), a polyisoprene (IR), a butyl rubber (IIR), an ethylene-propylene copolymer, a polyisobutylene-co-isoprene, a neoprene, a poly(ethylene-co-propylene), a poly(styrene-co-butadiene), a poly(styrene-co-isoprene), a poly(styrene-co-isoprene-co-butadiene), a poly(isoprene-co-butadiene), a poly(ethylene-co-propylene-co-diene), a polysulfide rubber, an acryl rubber, a urethane rubber, a silicone rubber, an epichlorohydrin rubber, a butyl rubber, and a halogenated butyl rubber, and any one or a mixture of two or more thereof may be used.

The rubber composition may, for example, include 0.1 parts by weight to 200 parts by weight, or 10 parts by weight to 120 parts by weight of a filler based on 100 parts by weight of the modified conjugated diene-based polymer of the present invention. The filler may particularly be, for example, a silica-based filler, particularly, wet silica (hydrated silicate), dry silica (anhydrous silicate), calcium silicate, aluminum silicate, or colloid silica. Preferably, the filler may be wet silica which has the most significant compatible effect of improving effect of destruction characteristics and wet grip. In addition, the rubber composition may further include a carbon black-based filler, if needed.

In another embodiment, if silica is used as the filler, a silane coupling agent for the improvement of reinforcing and low exothermic properties may be used together. Particular examples of the silane coupling agent may include bis(3-triethoxysilylpropyl)tetrasulfide, bis(3-triethoxysilylpropyl)trisulfide, bis(3-triethoxysilylpropyl)disulfide, bis(2-triethoxysilylethyl) tetrasulfide, bis(3-trimethoxysilylpropyl)tetrasulfide, bis(2-trimethoxysilylethyl)tetrasulfide, 3-mercaptopropyltrimethoxysilane, 3-mercaptopropyltriethoxysilane, 2-mercaptoethyltrimethoxysilane, 2-mercaptoethyltriethoxysilane, 3-trimethoxysilylpropyl-N,N-dimethylthiocarbamoyltetrasulfide, 3-triethoxysilylpropyl-N,N-dimethylthiocarbamoyltetrasulfide, 2-triethoxysilylethyl-N,N-dimethylthiocarbamoyltetrasulfide, 3-trimethoxysilylpropylbenzothiazolyltetrasulfide, 3-triethoxysilylpropylbenzolyltetrasulfide, 3-triethoxysilylpropylmethacrylatemonosulfide, 3-trimethoxysilylpropylmethacrylatemonosulfide, bis(3-diethoxymethylsilylpropyl) tetrasulfide, 3-mercaptopropyldimethoxymethylsilane, dimethoxymethylsilylpropyl-N,N-dimethylthiocarbamoyltetrasulfide, or dimethoxymethylsilylpropylbenzothiazolyltetrasulfide, and any one or a mixture of two or more thereof may be used. Preferably, the silane coupling agent may be bis(3-triethoxysilylpropyl)polysulfide or 3-trimethoxysilylpropylbenzothiazyltetrasulfide in consideration of the improving effect of reinforcing properties.

In addition, in the rubber composition according to an embodiment of the present invention, a modified conjugated diene-based polymer in which a functional group having high affinity with silica is introduced into an active part as a rubber component is used, and the mixing amount of a silane coupling agent may be smaller than a common case. Accordingly, the silane coupling agent may be used in an amount of 1 part by weight to 20 parts by weight, or 5 parts by weight to 15 parts by weight based on 100 parts by weight of silica, and within this range, effect as a coupling agent may be sufficiently exhibited, and the gelation of the rubber component may be prevented.

The rubber composition according to an embodiment of the present invention may be sulfur crosslinkable, and may further include a vulcanizing agent. The vulcanizing agent may particularly be a sulfur powder and may be included in an amount of 0.1 parts by weight to 10 parts by weight based on 100 parts by weight of a rubber component. With the amount in the above range, elasticity and strength required for a vulcanized rubber composition may be secured, and at the same time, a low fuel consumption ratio may be excellent.

The rubber composition according to an embodiment of the present invention may further include various additives used in a common rubber industry in addition to the above-described components, particularly, a vulcanization accelerator, a process oil, a plasticizer, an antiaging agent, a scorch preventing agent, a zinc white, stearic acid, a thermosetting resin, or a thermoplastic resin.

The vulcanization accelerator may use, for example, thiazole-based compounds such as 2-mercaptobenzothiazole (M), dibenzothiazyldisulfide (DM), and N-cyclohexyl-2-benzothiazylsulfenamide (CZ), or guanidine-based compounds such as diphenylguanidine (DPG), and may be included in an amount of 0.1 parts by weight to 5 parts by weight based on 100 parts by weight of the rubber component.

The process oil acts as a softener in a rubber composition and may include, for example, a paraffin-based, naphthene-based, or aromatic compound, and an aromatic process oil may be used in consideration of tensile strength and abrasion resistance, and a naphthene-based or paraffin-based process oil may be used in consideration of hysteresis loss and properties at a low temperature. The process oil may be included, for example, in an amount of 100 parts by weight or less based on 100 parts by weight of the rubber component. With the amount in the above-described range, the deterioration of tensile strength and low exothermic properties (low fuel consumption ratio) of the vulcanized rubber may be prevented.

The antiaging agent may include, for example, N-isopropyl-N'-phenyl-p-phenylenediamine, N-(1,3-dimethylbutyl)-N'-phenyl-p-phenylenediamine, 6-ethoxy-2,2,4-trimethyl-1,2-dihydroquinoline, or a condensate of diphenylamine and acetone at a high temperature, and may used in an amount of 0.1 parts by weight to 6 parts by weight based on 100 parts by weight of the rubber component.

The rubber composition according to an embodiment of the present invention may be obtained by mulling using a mulling apparatus such as a banbury mixer, a roll, and an internal mixer according to mixing prescription. In addition, a rubber composition having low exothermic properties and good abrasion resistance may be obtained by a vulcanization process after a molding process.

Therefore, the rubber composition may be useful to the manufacture each member for tires such as a tire tread, an under tread, a side wall, a carcass coating rubber, a belt coating rubber, a bead filler, a chafer, and a bead coating rubber, or to the manufacture of rubber products in various industries such as a dustproof rubber, a belt conveyor, and a hose.

Also, the present invention provides a tire manufactured using the rubber composition.

The tire may include a tire or a tire tread.

Hereinafter, the present invention will be explained in more detail referring to embodiments. However, the following embodiments are only for the illustration of the present invention, and the scope of the present invention is not limited thereto.

EXAMPLES

Example 1

To a 10 L autoclave reactor, 250 g of styrene, 750 g of 1,3-butadiene, 7,000 g of n-hexane, and 0.8 g of ditetrahydrofurylpropane as a polar additive were added, and the internal temperature of the reactor was elevated to 70° C. When the internal temperature of the reactor reached 60° C., 0.5 g of a solution in which n-butyllithium was dissolved in hexane by 1.53 wt % was injected into the reactor, and an adiabatic reaction with heating was performed. After about 40 minutes from the completion of the adiabatic reaction with heating, 10 g of N,N,N',N'-tetramethylethene-1,1-diamine was injected for capping the terminal of a polymer with N,N,N',N'-tetramethylethene-1,1-diamine. After 20 minutes, 1 g of bis(methyldimethoxysilylpropyl)-N-methylamine was injected, and the reaction was conducted for 30 minutes. Then, the polymerization reaction was quenched by using isopropyl alcohol, and 45 ml of a solution in which butylated hydroxytoluene (BHT) was dissolved in hexane as an antioxidant by 0.3 wt %, was added thereto. The polymer thus obtained was added to hot water heated using steam and stirred to remove solvents, followed by roll drying to remove remaining solvents and water to prepare a modified conjugated diene-based polymer.

Example 2

A modified conjugated diene-based polymer was prepared by conducting the same method as in Example 1 except for injecting the same amount of N,N,N',N'-tetraethylethene-1,1-diamine instead of N,N,N',N'-tetramethylethene-1,1-diamine in Example 1.

Example 3

A modified conjugated diene-based polymer was prepared by conducting the same method as in Example 1 except for injecting 1.2 g of bis(methyldiethoxysilylpropyl)-N-methylamine instead of 1 g of bis(methyldimethoxysilylpropyl)-N-methylamine in Example 1.

Example 4

A modified conjugated diene-based polymer was prepared by conducting the same method as in Example 1 except for injecting 1.2 g of 1-trimethylsilyl-2,2-dimethoxy-1-aza-2-silacyclopentane instead of 1 g of bis(methyldimethoxysilylpropyl)-N-methylamine in Example 1.

Example 5

A modified conjugated diene-based polymer was prepared by conducting the same method as in Example 1 except for injecting 0.7 g of N,N-diethylaminopropyltriethoxysilane instead of 1 g of bis(methyldimethoxysilylpropyl)-N-methylamine in Example 1.

Comparative Example 1

A modified conjugated diene-based polymer was prepared by conducting the same method as in Example 1 except for injecting 10 g of a mixture of 3-(2-pyrrolidinoethyl) styrene and 4-(2-pyrrolidinoethyl)styrene instead of N,N,N',N'-tetramethylethene-1,1-diamine, and not injecting bis(methyldimethoxysilylpropyl)-N-methylamine in Example 1.

Comparative Example 2

A modified conjugated diene-based polymer was prepared by conducting the same method as in Example 1 except for injecting 10 g of a mixture of 3-(2-pyrrolidinoethyl) styrene and 4-(2-pyrrolidinoethyl)styrene instead of N,N,N',N'-tetramethylethene-1,1-diamine in Example 1.

Comparative Example 3

A modified conjugated diene-based polymer was prepared by conducting the same method as in Example 1 except for not injecting N,N,N',N'-tetramethylethene-1,1-diamine in Example 1.

Comparative Example 4

A modified conjugated diene-based polymer was prepared by conducting the same method as in Example 1 except for injecting N,N,N',N'-tetramethylethane-1,1-diamine instead of N,N,N',N'-tetramethylethene-1,1-diamine in Example 1.

Experimental Example 1 le;.5qWith respect to each of modified or unmodified conjugated diene-based polymers prepared in Examples 1 to 5 and Comparative Examples 1 to 4, a weight average molecular weight (Mw, ×10³ g/mol), a number average molecular weight (Mn, ×10³ g/mol), molecular weight distribution (MWD), mooney viscosity (MV), and coupling efficiency were measured. The results are shown in Table 1 below.

The weight average molecular weight (Mw), and the number average molecular weight (Mn) were measured by gel permeation chromatography (GPC) analysis, and the molecular weight distribution (MWD, Mw/Mn) was obtained by the calculation from each of the measured molecular weights. Particularly, GPC was conducted using two columns of PLgel Olexis (Polymer Laboratories Co. Ltd.) and one column of PLgel mixed-C (Polymer Laboratories Co. Ltd.) in combination, newly replaced columns were all mixed bed type columns, and polystyrene (PS) was used as a GPC standard material for calculating the molecular weights.

The mooney viscosity (MV, (ML1+4, @100° C.) MU) was measured by using MV-2000 (ALPHA Technologies Co., Ltd.) using Large Rotor at a rotor speed of 2±0.02 rpm at 100° C. In this case, a specimen used was stood at room temperature (23±3° C.) for 30 minutes or more, and 27±3 g of the specimen was collected and put in a die cavity, and then, Platen was operated for measurement for 4 minutes.

The coupling efficiency utilized a value according to Mathematical Equation 1 below by distinguishing maximum peak molecular weights (Mp) according to GPC before and after modification.

$$\text{Coupling efficiency} = \frac{Mp \text{ after modification}}{Mp \text{ before modification}} \quad \text{[Mathematical Equation 1]}$$

TABLE 1

| Division | Example | | | | | Comparative Example | | | |
|---|---|---|---|---|---|---|---|---|---|
| | 1 | 2 | 3 | 4 | 5 | 1 | 2 | 3 | 4 |
| Mn | 32 | 31 | 29 | 33 | 33 | 22 | 24 | 27 | 26 |
| MWD | 1.71 | 1.72 | 1.73 | 1.68 | 1.65 | 1.50 | 1.78 | 1.69 | 1.72 |
| MV | 50 | 52 | 48 | 55 | 54 | 30 | 42 | 53 | 52 |
| Coupling efficiency | 2.0 | 1.9 | 1.7 | 2.3 | 1.7 | — | 1.2 | 1.8 | 1.5 |

Experimental Example 2

In order to comparatively analyze the physical properties of a rubber composition including each of modified or unmodified conjugated diene-based copolymers prepared in Examples 1 to 5 and Comparative Examples 1 to 4 and a molded article manufactured therefrom, tensile properties, abrasion resistance and wet skid resistance were measured, respectively, and the results are shown in Table 3 below.

1) Preparation of Rubber Specimen

By using each of modified or unmodified conjugated diene-based copolymers prepared in Examples 1 to 5 and Comparative Examples 1 to 4 as a raw rubber, mixing was performed according to the mixing conditions shown in Table 2 below. The raw material in Table 2 is represented by parts by weight based on 100 parts by weight of rubber.

TABLE 2

| Division | Raw material | Amount (parts by weight) |
|---|---|---|
| First stage mulling | Rubber | 100 |
| | Silica | 70 |
| | Coupling agent | 11.2 |
| | Process oil | 33.75 |
| | Zinc white | 3.0 |
| | Stearic acid | 2.0 |
| | Antioxidant | 2.0 |
| | Antiaging agent | 2.0 |
| | Wax | 1.0 |
| | Rubber accelerator | 1.75 |
| Second stage mulling | Sulfur | 1.5 |
| | Vulcanization accelerator | 1.5 |

Particularly, the rubber specimen was mulled via a first stage mulling and a second stage mulling. In the first stage mulling, a raw rubber (styrene-butadiene copolymer), a filler, an organosilane coupling agent, a process oil, a zinc white, stearic acid, an antioxidant, an antiaging agent, wax and an accelerator were mixed and mulled using a banbury mixer equipped with a temperature controlling apparatus. In this case, the temperature of the mulling apparatus was controlled to 140° C., and a first compound mixture was obtained at a discharge temperature of 140° C. to 160° C. In the second stage mulling, the first compound mixture was cooled to room temperature, and the first compound mixture, sulfur and a vulcanization accelerator were added to the mulling apparatus and mixed at a temperature of 50° C. or less to obtain a second compound mixture. Then, a curing process was performed at 160° C. to 180° C. for 20 to 30 minutes to manufacture a rubber specimen.

2) Tensile Properties

The tensile properties were measured by manufacturing each specimen for test and measuring tensile stress when elongated by 300% (300% modulus) of each specimen according to an ASTM 412 tensile test method. Particularly, measurement of tensile properties was performed by using a Universal Test machin 4204 tensile tester (Instron Co., Ltd.) at room temperature at a rate of 50 cm/min.

3) Abrasion Resistance

By using an Akron abrasion test apparatus, abrasion amount of a load of 6 pounds with 1,000 rotations was measured and indexed based on the resultant value of Comparative Example 3 according to Mathematical Equation 2. Abrasion amount is denominator, and with the increase of a index value, abrasion resistance becomes better.

$$\text{Abrasion index} = \left( \frac{\text{Standard abrasion value} - \text{Measured abrasion value}}{\text{Standard abrasion value}} \times 100 \right) + 100 \quad \text{[Mathematical Equation 2]}$$

4) Viscoelasticity Properties

Viscoelasticity properties were obtained by measuring tan δ while changing deformation at each measurement temperature (−60° C. to 60° C.) and a frequency of 10 Hz with a twist mode by using a dynamic mechanical analyzer (TA Co., Ltd.), and indexing based on the resultant value of Comparative Example 3 according to Mathematical Equations 3 and 4. If the tan δ index at a low temperature of 0° C. is high, it means that wet skid resistance is good, and if the tan δ index at a high temperature of 60° C. is high, it means that hysteresis loss is small and low rolling resistance (fuel consumption ratio) is excellent.

$$0° C. \text{ tan } \delta \text{ index} = \left( \frac{\text{Measured value} - \text{Standard value}}{\text{Standard value}} \times 100 \right) + 100 \quad \text{[Mathematical Equation 3]}$$

$$60° C. \text{ tan } \delta \text{ index} = \left( \frac{\text{Measured value} - \text{Standard value}}{\text{Standard value}} \times 100 \right) + 100 \quad \text{[Mathematical Equation 4]}$$

TABLE 3

| Division | | Example | | | | | Comparative Example | | | |
|---|---|---|---|---|---|---|---|---|---|---|
| | | 1 | 2 | 3 | 4 | 5 | 1 | 2 | 3 | 4 |
| Tensile properties | 300% modulus (kgf/cm²) | 132 | 133 | 128 | 131 | 129 | 106 | 114 | 110 | 107 |
| Abrasion resistance | Abrasion index | 101 | 100 | 102 | 101 | 103 | 85 | 95 | 100 | 99 |
| Viscoelasticity | tan δ @0° C. index | 102 | 103 | 101 | 102 | 102 | 80 | 102 | 100 | 94 |
| | tan δ @60° C. index | 105 | 105 | 104 | 106 | 105 | 85 | 103 | 100 | 95 |

As shown in Table 3, the modified conjugated diene-based polymers of Examples 1 to 5, which included a repeating unit derived from the modification monomer according to the present invention were found to have improved tensile properties and abrasion resistance, and markedly improved viscoelasticity properties when compared to modified or unmodified conjugated diene-based polymers of Comparative Examples 1 to 4, which did not include a repeating unit derived from the modification monomer of the present invention.

Particularly, though modified using the same modifier, the modified conjugated diene-based polymers of Example 1 and Example 2, which included a repeating unit derived from the modification monomer according to the present invention were found to have improved tensile properties and abrasion resistance, and particularly, markedly improved viscoelasticity properties when compared to Comparative Example 3, which did not include a repeating unit derived from the modification monomer of the present invention.

In addition, Example 1, which included a repeating unit derived from the modification monomer according to the present invention, was found to have markedly improved tensile properties, abrasion resistance, and viscoelasticity properties when compared to the modified conjugated diene-based polymer of Comparative Example 4, which was prepared under the same conditions except for the modification monomer.

On the contrary, Comparative Example 1, in which a styrene-based modification monomer was injected instead of the modification monomer according to the present invention and modification reaction by a modifier was not performed, was found to have very inferior tensile properties, abrasion resistance and viscoelasticity properties. Comparative Example 2, in which a styrene-based modification monomer was injected instead of the modification monomer according to the present invention and modification reaction by a modifier was performed, was found to have inferior tensile properties and abrasion resistance.

The invention claimed is:

1. A modification conjugated diene-based polymer comprising a repeating unit derived from a conjugated diene-based monomer and a repeating unit derived from a modification monomer represented by the following Formula 1:

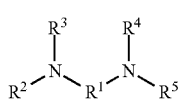

[Formula 1]

in Formula 1,
R¹ is a divalent hydrocarbon group of 1 to 10 carbon atoms, a heteroatom-containing divalent hydrocarbon group of 1 to 10 carbon atoms, or a linker represented by Formula 2,
R² to R⁵ are each independently hydrogen, a monovalent hydrocarbon group of 1 to 10 carbon atoms, or a heteroatom-containing monovalent hydrocarbon group of 1 to 10 carbon atoms, and
one or more of R¹ to R⁵ are required to be a hydrocarbon group including an unsaturated bond, where if R² to R⁵ do not include an unsaturated bond, R¹ is required to be a linker represented by the following Formula 2:

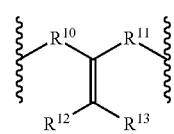

[Formula 2]

in Formula 2,
R$^{10}$ and R$^{11}$ are each independently a single bond, a divalent hydrocarbon group of 1 to 5 carbon atoms, or a heteroatom-containing divalent hydrocarbon group of 1 to 5 carbon atoms, and
R$^{12}$ and R$^{13}$ are each independently hydrogen, a monovalent hydrocarbon group of 1 to 5 carbon atoms, or a heteroatom-containing monovalent hydrocarbon group of 1 to 5 carbon atoms.

2. The modified conjugated diene-based polymer of claim 1, wherein the modified conjugated diene-based polymer further comprises a repeating unit derived from an aromatic vinyl monomer.

3. The modified conjugated diene-based polymer of claim 1, wherein the repeating unit derived from the modification monomer is comprised in a terminal part of the modified conjugated diene-based polymer.

4. The modified conjugated diene-based polymer of claim 1, wherein the modified conjugated diene-based polymer comprises a functional group derived from a modifier in a terminal part thereof.

5. The modified conjugated diene-based polymer of claim 4, wherein the modifier is an alkoxysilane-based modifier.

6. The modified conjugated diene-based polymer of claim 5, wherein the alkoxysilane-based modifier is a modifier represented by the following Formula 3:

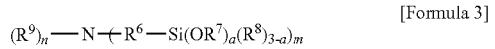

[Formula 3]

in Formula 3,
R$^6$ is an alkylene group of 1 to 10 carbon atoms, R$^7$ and R$^8$ are each independently an alkyl group of 1 to 10 carbon atoms, R$^9$ is hydrogen, an alkyl group of 1 to 10 carbon atoms, or a divalent, trivalent, or tetravalent alkylsilyl group which is unsubstituted or substituted with an alkyl group of 1 to 10 carbon atoms, a and m are each independently an integer selected from 1 to 3, and n is an integer selected from 0 to 2, where if n is 2, a plurality of R$^9$ groups may be the same or different.

7. The modified conjugated diene-based polymer of claim 6, wherein the modifier represented by Formula 3 is one selected from the group consisting of modifiers represented by the following Formulae 3-1, 3-2, 3-10, 3-11, 3-22 and 3-23:

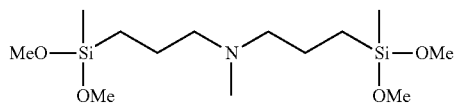

[Formula 3-1]

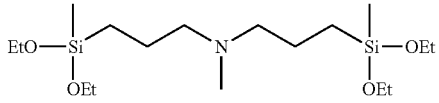

[Formula 3-2]

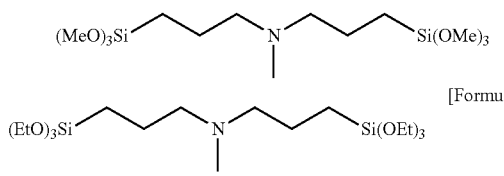

[Formula 3-10]

[Formula 3-11]

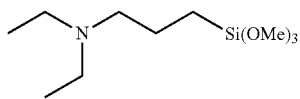

[Formula 3-22]

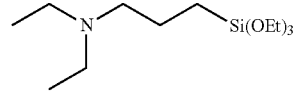

[Formula 3-23]

in Formulae 3-1, 3-2, 3-10, 3-11, 3-22 and 3-23 above, Me is a methyl group, and Et is an ethyl group.

8. A modified conjugated diene-based polymer comprising a repeating unit derived from a conjugated diene-based monomer and a repeating unit derived from a modification monomer represented by the following Formula 1, and comprising a functional group derived from a modifier represented by the following Formula 4 or Formula 5 at one terminal:

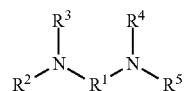

[Formula 1]

in Formula 1,
R$^1$ is a divalent hydrocarbon group of 1 to 10 carbon atoms, a heteroatom-containing divalent hydrocarbon group of 1 to 10 carbon atoms, or a linker represented by Formula 2,
R$^2$ to R$^5$ are each independently hydrogen, a monovalent hydrocarbon group of 1 to 10 carbon atoms, or a heteroatom-containing monovalent hydrocarbon group of 1 to 10 carbon atoms, and
one or more of R$^1$ to R$^5$ are required to be a hydrocarbon group including an unsaturated bond, where if R$^2$ to R$^5$ do not include an unsaturated bond, R$^1$ is required to be a linker represented by the following Formula 2:

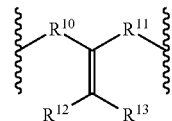

[Formula 2]

in Formula 2,
R$^{10}$ and R$^{11}$ are each independently a single bond, a divalent hydrocarbon group of 1 to 5 carbon atoms, or a heteroatom-containing divalent hydrocarbon group of 1 to 5 carbon atoms, and
R$^{12}$ and R$^{13}$ are each independently hydrogen, a monovalent hydrocarbon group of 1 to 5 carbon atoms, or a heteroatom-containing monovalent hydrocarbon group of 1 to 5 carbon atoms,

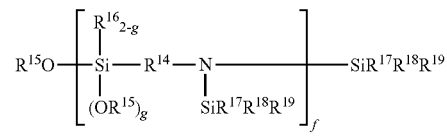

[Formula 4]

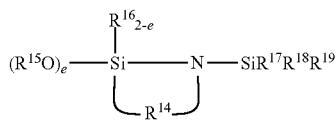

[Formula 5]

in Formulae 4 and 5,
$R^{14}$ is an alkylene group of 1 to 12 carbon atoms,
$R^{15}$ and $R^{16}$ are each independently an alkyl group of 1 to 20 carbon atoms or an aryl group,
$R^{17}$, $R^{18}$ and $R^{19}$ are each independently an alkyl group of 1 to 20 carbon atoms or an aryl group, or two thereof may be combined with each other to form a ring including a silicon atom to which two thereof are combined,
e is an integer of 1 to 2, g is an integer of 1 to 2, and f is an integer of 1 to 10.

9. The modified conjugated diene-based polymer of claim 8, wherein the modifier represented by Formula 4 or Formula 5 is one selected from the group consisting of N,N-bis(trimethylsilyl)aminopropylmethyldimethoxysilane, 1-trimethylsilyl-2,2-dimethoxy-1-aza-2-silacyclopentane, N,N-bis(trimethylsilyl)aminopropyltrimethoxysilane, N,N-bis(trimethylsilyl)aminopropyltriethoxysilane, N,N-bis(trimethylsilyl)aminopropylmethyldiethoxysilane, N,N-bis(trimethylsilyl)aminoethyltrimethoxysilane, N,N-bis(trimethylsilyl)aminoethyltriethoxysilane, N,N-bis(trimethylsilyl)aminoethylmethyldimethoxysilane and N,N-bis(trimethylsilyl)aminoethylmethyldiethoxysilane.

10. A method for preparing a modified conjugated diene-based polymer, the method comprising:
polymerizing conjugated diene-based monomers, or an aromatic vinyl-based monomer and a conjugated diene-based monomer, in a hydrocarbon solvent comprising an organometal compound, to prepare an active polymer which is coupled with an alkali metal (S1); and
reacting the active polymer and a modification monomer represented by the following Formula 1 for end-capping a terminal of the active polymer with the modification monomer (S2):

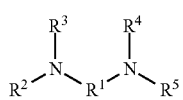

[Formula 1]

in Formula 1,
$R^1$ is a divalent hydrocarbon group of 1 to 10 carbon atoms, a heteroatom-containing divalent hydrocarbon group of 1 to 10 carbon atoms, or a linker represented by Formula 2,
$R^2$ to $R^5$ are each independently hydrogen, a monovalent hydrocarbon group of 1 to 10 carbon atoms, or a heteroatom-containing monovalent hydrocarbon group of 1 to 10 carbon atoms, and
one or more of $R^1$ to $R^5$ are required to be a hydrocarbon group including an unsaturated bond, where if $R^2$ to $R^5$ do not include an unsaturated bond, $R^1$ is required to be a linker represented by the following Formula 2:

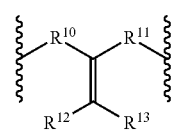

[Formula 2]

in Formula 2,
$R^{10}$ and $R^{11}$ are each independently a single bond, a divalent hydrocarbon group of 1 to 5 carbon atoms, or a heteroatom-containing divalent hydrocarbon group of 1 to 5 carbon atoms, and
$R^{12}$ and $R^{13}$ are each independently hydrogen, a monovalent hydrocarbon group of 1 to 5 carbon atoms, or a heteroatom-containing monovalent hydrocarbon group of 1 to 5 carbon atoms.

11. The method for preparing a modified conjugated diene-based polymer of claim 10, wherein the modification monomer in step (S2) is injected in an amount of 0.01 wt % to 10 wt % based on a total monomer amount of the conjugated diene-based monomer and the modification monomer, or the conjugated diene-based monomer, the aromatic vinyl-based monomer and the modification monomer.

12. The method for preparing a modified conjugated diene-based polymer of claim 10, wherein the method comprises a step (S3) of reacting the active polymer which is end-capped in step (S2) with a modifier.

13. The method for preparing a modified conjugated diene-based polymer of claim 12, wherein the modifier is an alkoxysilane-based modifier.

* * * * *